United States Patent [19]

Trautmann et al.

[11] Patent Number: 4,659,837

[45] Date of Patent: Apr. 21, 1987

[54] METHOD FOR THE PREPARATION OF 1,3-DISUBSTITUTED 4,5-CIS-DICARBOXY-2-IMIDAZOLIDONES

[75] Inventors: Walter Trautmann, Neustadt, Fed. Rep. of Germany; Friedrich Vogel, Mountain Lake, N.J.

[73] Assignee: BASF Aktiengesellschaft, Ludwigshafen, Fed. Rep. of Germany

[21] Appl. No.: 450,286

[22] Filed: Dec. 16, 1982

[30] Foreign Application Priority Data

Dec. 22, 1981 [DE] Fed. Rep. of Germany ....... 3150723

[51] Int. Cl.4 .......................................... C07D 233/32
[52] U.S. Cl. .................................................... 548/321
[58] Field of Search .......................................... 548/321

[56] References Cited

U.S. PATENT DOCUMENTS 2,489,232 11/1949 Goldberg et al. ................... 548/303
2,534,332 12/1950 Woodward .......................... 548/321

OTHER PUBLICATIONS

Bedel, C., Comptes Rendus, 177, 168–171 (1925).
Boon, W., J. Chem. Soc., 307 (1947).
Lob, G., Rec. Trav. Chim., 55, 859 (1936).
Fieser, M., et al., Reagents for Organic Synthesis, vol. 2, Wiley–Interscience, New York, 1969, p. 455.

Primary Examiner—Richard A. Schwartz
Attorney, Agent, or Firm—Rupert B. Hurley; David L. Hedden

[57] ABSTRACT

A process for the preparation of 1,3-disubstituted 4,5-cis-dicarboxy-2-imidazolidones useful as intermediates in the preparation of Vitamin H (biotin), said intermediates have the general formula

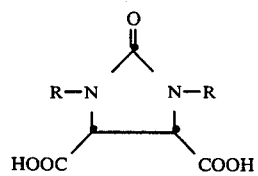

in which R is an aliphatic hydrocarbon radical having 1 to 8 carbon atoms, an aralkyl radical or an aromatic hydrocarbon radical, preferably an allyl radical or a benzyl radical, comprising reacting a defined diaminosuccinic acid with phosgene in the presence of an alkali metal hydroxide.

8 Claims, No Drawings

METHOD FOR THE PREPARATION OF 1,3-DISUBSTITUTED 4,5-CIS-DICARBOXY-2-IMIDAZOLIDONES

BACKGROUND OF THE INVENTION

1. Field of the Invention

The invention relates to an improved method for the preparation of 1,3-disubstituted 4,5-cis-dicarboxy-2-imidazolidones by reacting the corresponding substituted 2,3-diaminosuccinic acid with phosgene.

Description of the Prior Art

The products of this process, particularly the 1,3-diallyl- and 1,3-dibenzyl-substituted 4,5-cis-dicarboxy2-imidazolidones are important intermediate products for the preparation of Vitamin H, also referred to as biotin (see J.A.C.S. 100, 1978, page 1558, and U.S. Pat. No. 2,489,232). Said references describe a method for the preparation of said intermediates where the corresponding diaminosuccinic acid is reacted in a strongly alkaline solution (pH 13-14) to obtain the desired imidazolidones by adding dropwise a solution of phosgene in an inert organic solvent such as xylene or toluene, while simultaneously adding an alkali metal hydroxide. Since the reaction takes place in a twophase system of xylene/water and/or toluene/water in a strongly alkaline medium at pH >12, the 2,3-bis(allylamino)succinic acid reactant is present in the dissolved form.

This prior art method has serious drawbacks for technical implementation. Due to the high pH value of the reaction mixture, a large part of the phosgene is destroyed by hydrolysis. Therefore, a large excess of phosgene must be used. This in turn results in a large amount of undesirable salt production. Furthermore, problems with the reaction vessel materials result since the reaction medium is strongly corrosive as a result of the continuously increasing chloride ion concentration and since the work is also carried out at high pH (pH >12).

Furthermore, this prior art method requires the use of a phosgene solvent which is not miscible with water which reduces the reaction time and yield and further complicates processing. It has been found that conversion and yield fluctuate greatly when employing the known method. It was therefore the purpose of this invention to improve the prior art process in such a manner that the reaction can be carried out in a simpler and more economical manner with fewer problems concerning the materials of the reaction vessels.

SUMMARY OF THE INVENTION

Surprisingly, it was found that the N,N-disubstituted 2,3-diaminosuccinic acid in aqueous solution can be transformed with very good yield into the desired imidazolidones by simple gassing with phosgene, if a suitable pH range is maintained during the phosgenation.

Furthermore, it was found that the unreacted diaminosuccinic acid can be reclaimed essentially without loss if the reaction mixture is acidified in two stages during processing. Initially, the unreacted diaminosuccinic acid is separated by filtration at a pH of 3.5 to 4.5, and subsequently, the desired imidazolidones are extracted with ethyl acetate at a pH value of less than 1. It was further found that the desired imidazolidones are highly soluble in water-saturated ethyl acetate (approximately 100 grams/liter at 20° C.), whereas their solubility in dry ethyl acetate is very low (<10 grams/liter at 20° C.).

DETAILED DESCRIPTION OF THE INVENTION

The subject of this invention is a method for the preparation of 1,3-disubstituted 4,5-cis-dicarboxy-2-imidazolidone compounds having the formula:

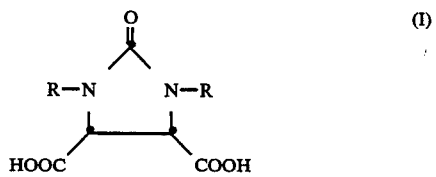

In this formula, R is an aliphatic hydrocarbon radical with 1-8 carbon atoms, an aralkyl radical, or an aromatic hydrocarbon radical, preferably an allyl radical or a benzyl radical obtained by reaction of diaminosuccinic acid compounds having the formula:

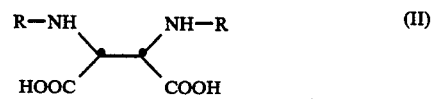

with phosgene in the presence of an alkali metal hydroxide, wherein

A. the diaminosuccinic acid of formula II is present in an aqueous suspension maintained at a temperature of 0° to 60° C., preferably 10° to 30° C. and is gassed with phosgene, while a suitable pH range is maintained;

B. the unreacted compound II is separated from the resultant reaction mixture, optionally by filtration, at a pH value of 3.5 to 4.5; and C. the remaining reaction mixture is extracted at a pH value of less than 1.

Presumably the pH value suitable for the reaction is predominantly a function of the solubility of compounds I and II, and thus determined by the respective substituents R. In each case a certain amount of compound II must be dissolved in the aqueous reaction solution so that reaction with the gaseous phosgene can take place. For compounds I or II in which R stands for an aliphatic hydrocarbon radical, the alkalinity range is between about pH 7 to about pH 11, specifically when R represents an allyl radical, at pH 7.5 to 8. For compounds I and/or II in which R stands for an aryl radical or an aralkyl radical, the optimum pH range is about pH 9.5 to pH 12.5, specifically when R represents benzyl, about pH 10.5 to pH 11. For every R, the pH range can be determined relatively simple by preliminary tests with a glass electrode.

It has been found that the yield of the reaction according to this invention can be further improved if the phosgenation is carried out in the presence of certain nitrogen compounds. Alternatively, this invention relates to a process wherein the gassing of compound II with phosgene is carried out in the presence of 1 to 10 percent by weight, based upon said compound, of a nitrogen compound selected from the group consisting of urea, thiourea, alkylated urea, alkylated thiourea, N,N-dialkylamides, N,N-dialkylcarbamates, hexamethylphosphoric acid triamide, and N-methyl-pyrrolidone, but preferably in the presence of urea.

The process of this invention is particularly advantageous if the filtrate is extracted with a water-miscible organic solvent such as ethyl acetate at a pH value of less than 1 and the water-containing ethyl acetate phase is subsequently dewatered by means of distillation so as to allow the imidazolidones of formula I to be obtained by crystallization out of dry ethyl acetate.

When employing this mode of operation the water contained in the ethyl acetate extract is removed by distillation at 70° C. The products of the process in the now dry ethyl acetate are of such high purity that a recrystallization is not required. Any impurities present remain dissolved in the ethyl acetate.

In a specific illustration of the process of the invention, one first suspends the diaminosuccinic acid in water and adjusts the pH value of the aqueous suspension to the previously determined optimum pH range by adding concentrated sodium hydroxide solution in a dropwise manner. Following this the suspension is gassed with phosgene. By the dropwise addition of concentrated sodium hydroxide solution, the pH value at all times is maintained accurately at the optimum range. By means of cooling, the reaction temperature is maintained in a range of 0° to 60° C., preferably 10° to 30° C. During the phosgenation the suspension gradually changes into a solution. After introducing 2 to 3 equivalents of phosgene, a nearly clear solution is obtained which contains little undissolved solids. For further processing the reaction mixture is initially acidified to a pH of 3.5 to 4.5, and unreacted starting materials are separated by means of filtration. Following this process, filtrate and washing water are adjusted to a pH value of less than 1 and the imidazolidone (I) is extracted with ethyl acetate according to known methods. The ethyl acetate extract is dewatered by distillation, whereupon the product can be crystallized and isolated from the dry ethyl acetate in an analytically pure state.

Using the process of this invention, the 1,3-disubstituted 4,5-cis-dicarboxy-2-imidazolidones of formula I required as very important intermediate products for the biotin synthesis can be produced in a very advantageous manner. Particularly for compounds I and II with R representing allyl, the method according to this invention overcomes all the disadvantages of the processes known from the cited prior art and, furthermore, offers a series of additional process engineering advantages. Thus, for example, the hydrolysis of phosgene during the phosgenation is largely suppressed in the pH range of this invention. As a result, the phosgene consumption is significantly less than in the method described in said prior art literature. Generally 1 to 5 moles, preferably 1 to 3.5 moles of phosgene are used per mole of diaminosuccinic acid. In the specified pH range the reaction can be carried out in a glass-lined vessel. Handling a solution of phosgene in organic solvents is avoided. The process according to this invention results in very well reproducible conversions and yields, and is safer and more economical.

The following examples illustrate the various aspects of the invention but are not intended to limit its scope. Where not otherwise specified throughout this specification and claims, temperatures are given in degrees centigrade and parts, percentages and proportions are by weight.

EXAMPLE 1

Preparation of 1,3-diallyl-4,5-cis-dicarboxy-2-imidazolidone by phosgenation of a diaminosuccinic acid having the formula (II) in which R is an allyl group wherein said diaminosuccinic acid is present in an aqueous suspension maintained at pH 7.5 to 8.

Meso-diallylaminosuccinic acid in the amount of 50 grams (0.219 moles) was mixed with 320 milliliters of water to form a suspension. By adding 1 milliliter of 50 percent aqueous sodium hydroxide solution, a pH value of 7.5 to 8 was established. This suspension at 20° C. was gassed beginning with 20 liters per hour of phosgene. On the whole, 73 grams (0.74 moles) of phosgene were introduced in a period of 50 minutes. During the phosgenation the pH value of the reaction mixture was maintained at 7.5 to 8 by adding dropwise 50 percent sodium hydroxide solution (a total of 95 milliliters). During the reaction the solid material increasingly went into solution. When almost all of the solid material was dissolved, the mixture was stirred at 20° C. and a pH of 8 to 9 for 30 minutes in order to render the flask contents phosgene free. Subsequently the reaction mixture was adjusted to a pH of 4.1 at 20° C. with concentrated hydrochloric acid. The precipitate was removed by suction and was washed three times with 200 milliliters of water. After drying, 14.8 grams (30 percent) of the mesodiallylaminosuccinic acid was isolated. Filtrate and washing water were (1) adjusted to a pH value of 0.5 percent with concentrated hydrochloric acid, (2) saturated with sodium chloride, and (3) extracted four times with 300 milliliters of ethyl acetate. The water-containing ethyl acetate extract was distilled to remove the water. Initially water was removed by distillation of the water-ethyl acetate at 70° C. The distillation was continued until the temperature of the distillate had increased to 77° C., the boiling point of pure ethyl acetate. Pure 1,3-diallyl-4,5-cis-dicarboxy-2-imidazolidone was obtained in the amount of 33.4 grams, melting point 161° C. to 163° C., by crystallization from the dewatered ethyl acetate extract which had been concentrated to 300 milliliters.

The yield based on reacted compound (II) was 86 percent of theory with a conversion of 70 percent.

EXAMPLE 2

(control)

Phosgenation, as in Example 1, with other pH values.

The test described in Example 1 was repeated except that the phosgenation was carried out at a pH value of 13 to 13.5 instead of 7.5 to 8. This resulted in 25.5 grams of unreacted meso-diallylaminosuccinic acid, that is, the conversion was only 49 percent, to produce 1,3-diallyl-4,5-cis-dicarboxy-2-imidazolidone in the amount of 23.9 grams.

EXAMPLE 3

(control)

The test described in Example 1 was repeated except that the phosgenation was carried out at a pH value of 5.0 instead of 7.5 to 8. This reaction resulted in 40 grams of unreacted meso-diallylamino succinic acid, that is the conversion amounted to only 20 percent. The product was obtained in the amount of 9.6 grams.

EXAMPLE 4

(control)

The test described in Example 1 was repeated except that the phosgenation was carried out at a pH value of 6.5 to 7 instead of 7.5 to 8. This resulted in a yield of 25.0 grams of compound (II), that is, the conversion was only 50 percent. The desired product was obtained in the amount of 24 grams.

EXAMPLE 5

Preparation of 1,3-dibenzyl-4,5-cis-dicarboxy-2-imidazolidone by reacting a diaminosuccinic acid of formula (II) in which R represents a benzyl group with phosgene wherein said acid of formula (II) is present in an aqueous suspension maintained at a pH of 10.5 to 11.

Meso-dibenzylaminosuccinic acid 50 grams (0.152 moles) was suspended in 950 milliliters of water. The pH value of this suspension was adjusted to 10.5 by means of 2 milliliters of 50 percent sodium hydroxide solution. Subsequently, the suspension was gassed with approximately 20 liters per hour of phosgene at 20° C. In 20 minutes a total of 30 grams (0.303 moles) of phosgene were introduced. The pH was monitored continuously and was maintained at 10.5 to 11 by adding 50 percent sodium hydroxide solution in a dropwise manner (a total of 57 milliliters). By cooling, the internal temperature was maintained at 25° to 30° C. Subsequently the reaction mixture was stirred at room temperature for 30 minutes. Following this time the flask contents were phosgene-free. The product was then acidified with concentrated hydrochloric acid to a pH of 3.5 at 20° C., the precipitate was (1) filtered, (2) washed three times with 200 milliliters of water, and (3) washed three times with 200 milliliters of anhydrous ethyl acetate. After drying, 19.8 grams (40 percent) of meso-dibenzylaminosuccinic acid were obtained. The filtrate and washing water were combined and adjusted to a pH of 0 with concentrated hydrochloric acid, then saturated with sodium chloride and extracted three times with a total of 1000 milliliters of ethyl acetate. The combined ethyl acetate phases were dewatered by distillation. The azeotrope consisting of water and ethyl acetate initially was distilled off at a boiling point of 70° C. and pure ethyl acetate was distilled off at the end at a boiling point at 77° C. From the ethyl acetate phase, the water was removed in this manner to obtain 21.8 grams of 1,3-dibenzyl-4,5-cis-dicarboxy-2-imidazolidone having a melting point of 176° C. to 177° C. The yield is 67 percent of theory with a conversion of 60 percent.

EXAMPLE 6

(control)

Phosgenation as in Example 5 with other pH values.
The test described in Example 5 was repeated except that the phosgenation was carried out at a pH value of 7.5 to 8 instead of pH 10.5 to 11. This resulted in 32.5 grams of unreacted meso-dibenzylaminosuccinic acid, that is the conversion was only 35 percent. No 1,3-dibenzyl-4,5-cis-dicarboxy-2-imidazolidone could be isolated.

EXAMPLE 7

(control)

The test described as in Example 5 was repeated except that the phosgenation was carried out at a pH value of 13 instead of 10.5 to 11. There was obtained 23.2 grams of unreacted meso-dibenzylaminosuccinic acid and 13.2 grams of 1,3-dibenzyl-4,5-cis-dicarboxy-2-imidazolidone having a melting point of 177° C. The yield was 45 percent of theory with a conversion of 54 percent.

EXAMPLE 8

Preparation of 1,3-dibenzyl-4,5-cis-dicarboxy-2-imidazolidone in the presence of urea.

Meso-dibenzylaminosuccinic acid 50 grams (0.152 moles) was suspended in 950 milliliters of water. After adding 2.5 grams of urea, the pH value was adjusted to 10.5 with 2 milliliters of 50 percent sodium hydroxide solution. The suspension was gassed with approximately 20 liters of phosgene per hour at 20° C. A total of 30 grams (0.303 moles) of phosgene were introduced within 20 minutes. The pH value was monitored continuously and was maintained at 10.5 to 11 by adding 50 percent sodium hydroxide solution in a dropwise fashion (a total of 57 milliliters). By cooling, the internal temperature was maintained at 25° C. to 30° C.

Subsequently the reaction mixture was stirred at room temperature for 30 minutes. Following this step the flask contents were phosgene-free. With concentrated hydrochloric acid, the product was acidified to a pH of 3.5 at 20° C. The precipitate which forms was filtered, washed 3 times with 200 milliliters of water, and subsequently washed three times with 200 milliliters of anhydrous ethyl acetate. After drying, 22.6 grams (45 percent) of the mesodibenzylaminosuccinic acid were isolated, filtrate and washing water were combined and adjusted to a pH of 0 with concentrated hydrochloric acid, then saturated with sodium chloride and extracted three times with a total of 1000 milliliters of ethyl acetate. The combined ethyl acetate phases were concentrated until dry. This resulted in 26.7 grams (91 percent) of crude product from which 22.6 grams of 1,3-dibenzyl-4,5-cis-dicarboxy-2-imidazolidone having a boiling point of 175° to 176° C. were obtained by recrystallization from ethyl acetate. This corresponds with a yield of 77 percent of theory with a conversion of 55 percent.

EXAMPLE 9

(control)

Phosgenation as in Example 8 with other pH values.
The test described under A was repeated except that the phosgenation was carried out with a pH value of 7.5 to 8 instead of 10.5 to 11.

This resulted in 33.3 grams of unreacted said succinic acid as well as 1.6 grams of 1,3-dibenzyl-4,5-cis-dicarboxy-2-imidazolidone. The yield was only 9 percent of theory with a conversion of only 33 percent.

While this invention has been described with reference to certain specific embodiments, it will be recognized by those skilled in the art that many variations are possible without departing from the scope and spirit of the invention, and it will be understood that it is intended to cover all changes and modifications of the invention disclosed herein for the purpose of illustration which do not constitute departure from the spirit and scope of the invention.

The embodiments of the invention in which an exclusive privilege or property is claimed are defined as follows:

1. A process for the preparation of a 1,3-disubstituted 4,5-cis-dicarboxy-2-imidazolidone having the formula

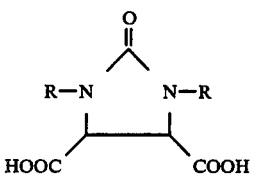

in which R stands for an aliphatic hydrocarbon radical with 1 to 8 carbon atoms, or an aromatic hydrocarbon radical, comprising:

(A) reacting a diaminosuccinic acid compound having the formula

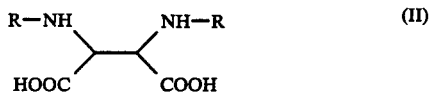

with phosgene in the presence of an alkali metal hydroxide, wherein when R is an aliphatic hydrocarbon radical with 1 to 8 carbon atoms said diaminosuccinic acid is present as an aqueous suspension maintained at a pH of about 7 to about 11 and a temperature of 0° C. to 60° C., and when R is an aromatic hydrocarbon radical, said diamino succinic acid is present as an aqueous suspension maintained at a pH of about 9.5 to about 12.5 and a temperature of 0° C. to 60° C., and wherein said diaminosuccinic acid is gassed with phosgene to obtain a reaction mixture containing the desired reaction product (I), (B) separating said unreacted compound (II) from the resultant reaction solution at a pH of 3.5 to 4.5, (C) extracting said reaction mixture with a water-miscible organic solvent at a pH value of less than 1.0 to recover compound (I).

2. The process of claim 1 wherein the R group attached to the diaminosuccinic acid (II) represents an allyl group and the diaminosuccinic acid is gassed with phosgene while said acid is present in an aqueous suspension maintained at a pH value of 7.5 to 8.

3. The process of claim 1 wherein the R group attached to the diaminosuccinic acid (II) represents a benzyl group, and the diaminosuccinic acid is gassed with phosgene while said acid is present in an aqueous suspension maintained at a pH value of 10.5 to 11.

4. The process of claim 1 wherein the diaminosuccinic acid (II) is gassed with phosgnene at a temperature of 10° C. to 30° C.

5. The process of claim 2 wherein the diaminosuccinic acid (II) is gassed with phosgene at a temperature of 10° C. to 30° C.

6. The process of claim 3 wherein the diaminosuccinic acid (II) is gassed with phosgene at a temperature of 10° C. to 30° C.

7. The process of claim 4 wherein the gassing of compound II with phosgene is conducted in the presence of 1 to 10 percent by weight of a nitrogen compound, based upon said diaminosuccinic acid (II) wherein said nitrogen compound is selected from the group consisting of urea, thiourea, N,N-dialkylamides, N,N-dialkylcarbamates, hexamethyl phosphoric acid triamide, and N-methyl-pyrrolidone.

8. The process of claim 7 wherein said process is conducted in the presence of urea, said filtrate is extracted with ethyl acetate, the water-containing ethyl acetate phase obtained is subsequently dewatered by means of distillation, and said imidazolidones (I) are allowed to crystallize out of the dry ethyl acetate.

* * * * *